(12) United States Patent
Yao et al.

(10) Patent No.: US 6,512,149 B2
(45) Date of Patent: Jan. 28, 2003

(54) METHOD FOR REMOVING BUTYL GROUPS FROM BUTYL PHENOL COMPOUNDS

(75) Inventors: Kazuhiko Yao, Wakayama (JP);
Mitsuhiro Higashi, Wakayama (JP);
Kenji Ekawa, Wakayama (JP)

(73) Assignee: Honshu Chemical Industry Co., Ltd., Wakayama (JP)

( * ) Notice: Subject to any disclaimer, the term of this patent is extended or adjusted under 35 U.S.C. 154(b) by 0 days.

(21) Appl. No.: 09/834,335

(22) Filed: Apr. 13, 2001

(65) Prior Publication Data

US 2002/0007092 A1 Jan. 17, 2002

(30) Foreign Application Priority Data

Apr. 13, 2000 (JP) ........................................ 2000-112249

(51) Int. Cl.[7] .............................................. C07C 37/00
(52) U.S. Cl. ........................................ 568/805; 568/730
(58) Field of Search .................................. 568/730, 805

(56) References Cited

U.S. PATENT DOCUMENTS

| 1,747,604 | A | * | 2/1930 | Schollkopf |
| 2,382,506 | A | * | 8/1945 | Schulze |
| 2,435,038 | A | * | 1/1948 | Gilbert |
| 2,514,960 | A | * | 7/1950 | Luten |
| 3,091,646 | A | * | 5/1963 | Leston |
| 4,110,544 | A | * | 8/1978 | Goodwin |
| 4,205,187 | A | * | 5/1980 | Cardenas |
| 5,099,076 | A | * | 3/1992 | Takahashi |
| 5,324,868 | A | * | 6/1994 | Inaba |

* cited by examiner

*Primary Examiner*—Michael L. Shippen
(74) *Attorney, Agent, or Firm*—Knobbe, Martens Olson & Bear LLP

(57) ABSTRACT

By bringing a p-butylphenol compound or m-butylphenol compound in the gas phase into contact with a solid acid catalyst, i.e., a silica-alumina catalyst or alumina catalyst while heating, butyl groups are removed from the butylphenol compound and at the same time, highly purified isobutylene is recovered.

15 Claims, No Drawings

METHOD FOR REMOVING BUTYL GROUPS FROM BUTYL PHENOL COMPOUNDS

BACKGROUND OF THE INVENTION

1. Field of the Invention

The present invention relates to a method for removing butyl groups from a butylphenol compound.

More specifically, the present invention relates to a method for removing butyl groups from a butylphenol compound using a solid acid catalyst in the gas phase.

2. Description of the Related Art

Methods for removing butyl groups from butylphenol compounds to produce phenol compounds are conventionally known. For example, Japanese Patent Publication No. S49-39659 describes a method for isolating and recovering highly purified m-tert-butylphenol, in which a silica alumina solid acid catalyst is added to a mixture of m- and p-tert-phenols, or a mixture of o-, m- and p-tert-phenols, in the liquid phase to remove butyl groups from o- and p-tert-butylphenols. Japanese Patent Application Laid-open S52-71422 discloses a method for producing highly purified m-cresol and p-cresol, in which in order to isolate m-cresol and p-cresol from a mixture of m- and p-cresols, said mixture is reacted with isobutylene to obtain corresponding butylated cresols, after which these cresols are isolated by distillation, and butyl groups are removed from the resulting mono- and di-tert-butyl-m-cresols or mono- or di-tertbutyl-p-cresol in the liquid phase in the presence of a sulfuric acid catalyst.

Furthermore, Japanese Patent Application Laid-open No. H5-51337 discloses a method for producing highly purified m-tert-butylphenol, in which butyl groups of p-tert-butylphenol in a mixture of m-tert-butylphenol and p-tert-butylphenol are selectively removed in the liquid phase in the presence of a catalyst consisting of an active white clay and a small amount of a basic substance such as an alkaline metal.

However, the reactions in these known methods for removing butyl groups take place in the liquid phase and have to be carried out in the presence of a strong acid, such as sulfuric acid and sulfonic acid, and at a high temperature since butyl groups bonding with a phenol compound at the para position and meta position in particular are more difficult to remove than those bonding at the ortho position. Thus, the equipment for the reaction, such as the reaction vessel, tends to corrode so that the material for the equipment is limited. Further, the recovered isobutylene contains impurities primarily attributed to the catalyst so that the isobutylene is not pure enough to reuse as raw material isobutylene for a butylation reaction and another purification is required.

In removing butyl groups in the presence of a solid acid catalyst such as active white clay, the reaction time is long and a catalyst filtration process is required. Furthermore, the recovered isobutylene causes similar problems as mentioned above for organic acid catalysts.

SUMMARY OF THE INVENTION

Accordingly, the present invention is intended to solve the abovementioned problems associated with conventional methods for removing butyl groups in the liquid phase. Namely, an object of the present invention is to provide a method for easily removing butyl groups from butylphenol compounds, in particular, p- and m-tert-butylphenols in a high yield on an industrial scale. Another object of the present invention is to provide a method for removing butyl groups from butylphenol compounds in which the recovered isobutylene is of high purity and does not require another purification to reuse as raw material isobutylene for a butylation reaction or the like.

The present invention provides a method for removing butyl groups from a butylphenol compound, characterized in that the butylphenol compound in the gas phase is brought into contact with a solid acid catalyst while heating.

DETAILED DESCRIPTION OF THE PREFERRED EMBODIMENT

Examples of the butylphenol compound used in the present invention include those in which the tert-butyl group is bound to phenol or an alkyl phenol compound such as o-cresol, m-cresol, p-cresol, 2,3-xylenol, 2,4-xylenol, 2,5-xylenol, 2,6-xylenol, 3,4-xylenol, 3,5-xylenol. More precisely, they include o-tert-butylphenol, m-tert-butylphenol, p-tert-butylphenol, 2,4-di-tert-butylphenol, 2,5-di-tert-butylphenol, 2,6-di-tert-butylphenol, 2-tert-butyl-p-cresol, 2,6-di-tert-butyl-p-cresol, 2, 4-di-tert-butylmetacresol, and 6-tert-butyl-2,4-xylenol. In particular, p-tert-butylphenol, m-tert-butylphenol, 2,4-di-tert-butyl-m-cresol, and 2,6-di-tert-butyl-p-cresol are preferable.

A solid acid of strong acidity is preferable as a solid acid catalyst used in the present invention. More precisely, silica-alumina catalyst or alumina catalyst is used. A preferable silica-alumina catalyst is a synthetic amorphous silica-alumina catalyst. Its $SiO_2/Al_2O_3$ ratio is not specifically limited. Any readily available alumina-containing product having an alumina content from as low as about 12% to as high as about 25% can be used. The form of these catalysts upon use is not limited. As an alumina catalyst, γ-alumina is preferably used. However, cylindrically molded particles having an approximate dimension of (height: 1–10 mm)× (diameter: 1–10 mm) are used because of less variation in the catalytic strength of the molded particles and for other reasons.

The reaction to remove butyl groups is carried out by bringing a butylphenol compound in the gas phase into contact with a solid acid catalyst while heating. The butylphenol raw material used in the present invention can be a single butylphenol compound, a mixture of butylphenol compounds or a mixture of phenol compounds containing a butylphenol compound as the major component.

Examples of these mixtures include butylphenol compounds which are present in the reaction system upon the production of 4,4'-biphenol by removing butyl groups from crude or purified 3,3',5,5'-tetra-tert-butyl-biphenol produced by dimerizing 2,6-di-tert-butylphenol by oxidation, or butylated cresol compounds upon the production of highly purified m-cresol and p-cresol by reacting a mixture of m- and p-cresols with isobutylene, isolating the resulting corresponding butylated cresols, and removing butyl groups from them. Further, the butylphenol raw material can be diluted with an aromatic hydrocarbon, water, nitrogen or the like for the reaction. These diluting agents can be mixed in advance with the butylphenol raw material and then fed into a reaction vessel, or fed into the vessel separately. Phenol is preferable as a diluting agent because it lowers the coagulation point of the butylphenol raw material and has no adverse effect on the reaction. Preferably, phenol is admixed in advance with the butylphenol raw material, and then fed into the reaction vessel.

The amount of diluting agent to be added is generally between 30 wt % and 70 wt %/70 wt % and 30 wt % for phenol/butylphenol compound.

Further, a small amount of water is preferably added as a diluting agent to moderate the reduction in the removed rate of butyl groups due to deterioration of the solid acid catalyst with time (decoking). This water is preferably fed into the reaction vessel separately from the butylphenol raw material or a mixture of the butylphenol raw material and phenol because water and the butylphenol raw material are immiscible.

The reaction temperature increases if too much water is added, but the decoking effect by adding water will not occur if too little water is added. Accordingly, the preferable amount of water is 30–50 wt % of the supplied liquid (butylphenol raw material+phenol+water).

The type of gas phase reaction mode is not specifically limited and any gas-solid catalyst reaction vessel, such as a batch, fixed-bed or fluid-bed mode reactor can be used. However, fixed-bed mode is preferable for reasons economy, including low equipment cost. The reaction temperature is in the range of 200° C. to 500° C., preferably 200° C. to 400° C., more preferably 250° C. to 350° C. because reduction in the removed of butyl group is small if the temperature is lower than 200° C. and the catalyst function decreases if the temperature is higher than 600° C. The reaction pressure is not specifically limited, however a normal pressure is preferable.

Generally, at the abovementioned range of temperature and pressure, the reaction for removing butyl groups is completed instantly upon gas phase contact with the catalyst.

In the present invention, the method for feeding a raw material mixture into the reaction vessel is not specifically limited. For example, the mixture can be fed via a raw material preheating vessel and a vaporization vessel from the upper part of the reaction vessel. The feed rate is preferably in a range of 0.01–10 g/cc/hr, more preferably 0.1–1.0 g/cc/hr, as the liquid headspace velocity (LHSV) for the butylphenol raw material standard. If the feed rate is too slow, the amount of by-products increases due to isomerization reaction of the butylphenol raw material. If the rate is too fast, the butyl group removed rate decreases.

Water, a diluting agent, which can be fed to the reaction vessel separately from the raw material is generally fed to the reaction vessel as steam via a vaporization vessel in the same manner as described for the raw material mixture. The feed rate is about 0.2–0.4 g/cc/hr as the liquid head space velocity (LHSV).

For a fixed-bed mode reactor, the vessel is preferably filled in advance with a molded solid acid catalyst. Generally, activation treatment is preferably carried out with an inert gas, such as nitrogen gas, at 250–500° C. for about 5 hours before the reaction for removal of water from and activation of the catalyst.

Under the abovementioned conditions, butyl groups are readily removed from a butylphenol compound such as a tert-butylphenol compound by bringing the compound into contact with the abovementioned catalyst, and isobutylene and phenol compounds can be isolated. The reaction product is condensed liquefied by using a cooling tube or the like to recover phenol compounds lacking butyl groups at o-, m- and p-positions at a highly selective rate as well as highly purified isobutylene.

The butyl group removal rate is generally about 80–95% in the early stages of the reaction but decreases as the reaction time lapses. Further, the recovered isobutylene generally is of a 90–100% purity, occasionally contains a trace amount of isobutane or the like as a by-product, but does not contain corrosive harmful trace impurities such as sulfur compounds. Therefore, this isobutylene can generally be used as is without further purification as an isobutylene raw material, for example, for butylation of phenol compounds.

Further, in the present invention, the activity of the catalyst is slow so that the reaction for removing butyl groups can be continued, for example, for more than 400 hours on an industrial scale and the catalyst can be easily reactivated by regeneration. Further, the purity of the recovered isobutylene does not decrease when produced using this regenerated catalyst.

EXAMPLE

The present invention will be explained more in detail by the following examples.

In the present invention, the butyl group removed rate is expressed by the following formula.

Butyl group removal rate (%)={(number of moles of butyl groups in the reaction product)/(number of moles of total phenols in the reaction product)}/{(number of moles of butyl groups in raw material)/(number of moles of total phenols in raw material)}

Example 1

A vertical reaction tube (diameter: ½ inch, length: 40 cm) equipped with a raw material preheating vessel, vaporization vessel and Dimroth condenser for reaction products was used. An amorphous silica-alumina catalyst in the form of cylindrically molded particles 25 ml (N632HN, a product of Nikki Chemical Corp.) was filled into this reaction tube and heated under a nitrogen gas flow to activate the catalyst. Then, a raw material mixture consisting of a 70 wt % butylphenol composition containing 98 wt % p-tert-butylphenol and 30 wt % phenol was fed via the preheating vessel and the vaporization vessel from the top of the reaction tube. The reaction was carried out at 280° C. under normal pressure at a LHSV of 0.49 hr$^{-1}$ for the raw material mixture (at a LHSV of 0.34 hr$^{-1}$ for p-tert-butylphenol standard).

After 45 hours of reaction, the liquid reaction product and reaction product gas were sampled and analyzed by gas chromatography. Results showed that the reaction product comprised 90.5 wt % phenol, 0.3 wt % o-tert-butylphenol, and 8.8 wt % p-tert-butylphenol, and the butyl group removed rate was 90.5%.

On the other hand, the reaction product gas was isobutylene having a purity of 98.8 wt %, which did not contain any corrosive compounds such as sulfur oxides.

Example 2

An experiment was carried out as described in Example 1, except that a butylphenol composition containing 75 wt % p-tert-butylphenol (PTBP), 9 wt % m-tert-butylphenol (MTBP), and 3 wt % o-tert-butylphenol (OTBP) was used instead of the butylphenol composition containing 98 wt % p-tert-butylphenol, and the reaction was carried at a LHSV of 0.71 hr$^{-1}$ for the raw material mixture (at a LHSV of 0.5 hr$^{-1}$ for p-tert-butylphenol standard).

After 30 hours of reaction, the liquid reaction product was sampled and analyzed by gas chromatography. Results showed that the reaction product comprised 82 wt % phenol, 9.7 wt % PTBP, 7.3 wt % MTBP, and 0.7 wt % OTBP, and the butyl group removed rate was 81%. The raw material mixture was further continuously fed to carry out the reaction under the abovementioned conditions. After 360 hours of reaction, the liquid reaction product and reaction product gas were sampled and analyzed by gas chromatography. Results showed that the reaction product comprised 66 wt % phenol, 23.7 wt % PTBP, 8.6 wt % MTBP, and 0.7 wt % OTBP, and the butyl group removed rate was 61%.

On the other hand, the reaction product gas was isobutylene having a purity of 99.8 wt %, which did not contain any corrosive compounds such as sulfur oxides.

Example 3

An experiment was carried out as in Example 2, in which in addition to the raw material mixture, water was fed to the reaction tube through the preheating vessel and the vaporization vessel into the top of the reaction tube, from a feed tube different from that for the raw material mixture. The LHSV for the raw material mixture is 0.71 hr$^{-1}$ (at a LHSV of 0.34 hr$^{-1}$ for p-tert-butylphenol standard) and the LHSV for water was 0.3 hr$^{-1}$. Otherwise, the experiment was carried out in the same manner as described in Example 2.

After 7 hours of reaction, the liquid reaction product was sampled and analyzed by gas chromatography. Results showed that the butyl group removed rate was 62%. On the other hand, the reaction product gas was isobutylene having a purity of 99.8 wt %, which did not contain any corrosive compounds such as sulfur oxides.

Example 4

The reaction was carried out as described in Example 3, in which feeding of the raw material mixture and water to the reaction tube was stopped when the butyl group removed rate became less than 60%, and the catalyst was regenerated by increasing the temperature up to 500° C. first under a nitrogen flow, then under air. Then, the reaction for removing butyl groups as described in Example 3 was repeated. Immediately after the start of the reaction, the liquid reaction product was sampled and analyzed by gas chromatography. Results showed that the butyl group removed rate was 85%.

The raw material mixture was further continuously supplied to carry out the reaction under the abovementioned conditions. After 500 hours of reaction, the liquid reaction product and reaction product gas were sampled and analyzed by gas chromatography. Results showed that the butyl group removed rate was 60%. On the other hand, the reaction product gas was isobutylene having a purity of 99.8 wt %, which did not contain any corrosive compounds such as sulfur oxides.

Example 5

An experiment was carried out as described in Example 1, in which a raw material mixture consisting of a 72 wt % butyl-paracrezol composition containing 97.5 wt % 2,6-di-tert-butylphenol and 28 wt % phenol was used instead of the raw material mixture consisting of the 30 wt % butylphenol composition containing 98 wt % p-tert-butylphenol and 30 wt % phenol.

The reaction was carried out as described in Example 1, except that the LHSV was 0.49 hr$^{-1}$ for the raw material mixture (at a LHSV of 0.35 hr$^{-1}$ for 2,6-di-tert-butyl-paracresol standard).

After 45 hours of reaction, the liquid reaction product and reaction product gas were sampled and analyzed by gas chromatography. Results showed that the reaction product comprised 42 wt % phenol, 46 wt % p-cresol, 5 wt % 2,6-di-tert-butyl-paracresol, and 3 wt % 2-tert-butyl-p-cresol, and the butyl group removed rate was 92.8%. On the other hand, the reaction product gas was isobutylene having a purity of 99.0 wt %, which did not contain any corrosive compounds such as sulfur oxides.

Comparative Example

A butylphenol composition (250 g) containing 98 wt % p-tert-butylphenol and 0.5 g of p-toluene sulfonic acid, a catalyst, were placed in a four-naked flask fitted with a stirring device, a thermometer and a column filled to a height of 10 cm with stainless steal helipack, and then heated.

After reaction at 220° C. for about 10 hours, 137 g of phenol were distilled off. The butyl group removed rate was 80%. On the other hand, results of gas chromatography showed that the reaction product gas is isobutylene, which contained 0.1 wt % $SO_2$.

Further, after the reaction, 25 g of liquid was left at the bottom of the flask. The liquid was strongly acidic with a pH of 2.

Effectiveness of the Invention

In the method for removing butyl groups from a butylphenol compound according to the present invention, butyl groups are removed by bringing the butylphenol compound in the gas phase into contact with a solid acid catalyst so that the reaction can be instantly completed and the butyl group removed rate is high, which can easily applied to continuous process on an industrial scale. Furthermore, the recovered isobutylene is of high purity and does not contain any harmful trace impurities, such as sulfur compounds, so that it can be reused as an isobutylene raw material for butylation of phenol compounds.

Further, the activity of the catalyst decreases slowly, so that a continuous reaction for removing butyl groups for more than 400 hours is possible on an industrial scale, and the catalyst can be easily reactivated by regeneration. Further, the use of this regenerated catalyst does not lower the purity of the recovered butylene.

What is claimed is:

1. A method for removing tert-butyl group from a tert-butylphenol compound, comprising the steps of:
   preparing a raw material mixture of phenol and a tert-butylphenol compound wherein a ratio of phenol/tert-butylphenol compound is from 30 wt %/70 wt % to 70 wt %/30 wt %; and
   contacting the raw material mixture in a gas phase with a solid acid catalyst under heat to remove tert-butyl group from the tert-butylphenol compound.

2. The method according to claim 1, wherein the tert-butylphenol compound is p-t-butylphenol or m-t-butylphenol.

3. The method according to claim 1, further comprising recovering butylene from which tert-butyl group is removed.

4. The method according to claim 3, wherein the recovered butylene is purified isobutylene.

5. The method according to claim 1, wherein the solid acid catalyst is a silica-alumina catalyst or alumina catalyst.

6. The method according to claim 1, wherein the tert-butylphenol compound is a tert-butylphenol compound present in a reaction system where 3,3',5,5'-tetra-tert-butylbiphenol is subjected to removal of tert-butyl group.

7. The method according to claim 1, wherein the removal of tert-butyl group is conducted at a temperature of 200° C.–500° C.

8. The method according to claim 1, further comprising adding water to the tert-butylphenol compound for decoking.

9. The method according to claim 1, wherein the tert-butylphenol compound is contacted with the solid acid catalyst at a liquid head space velocity (LHSV) of 0.01–10 g/cc/hr.

10. The method according to claim 3, wherein the butylene has a purity of 95–100%.

11. The method according to claim 1, wherein the removal of tert-butyl group is conducted at a tert-butyl group removal rate of 80–95%.

12. The method according to claim 1, wherein tert-butyl group at any position is removed.

13. The method according to claim 1, wherein the removal of tert-butyl group is conducted at a temperature of 250° C.–350° C.

14. The method according to claim 1, wherein the tert-butylphenol compound is contacted with the solid acid catalyst at a liquid head space velocity (LHSV) of 0.1–1.0 g/cc/hr.

15. The method according to claim 8, wherein the water is added at a liquid head space velocity (LHSV) of 0.2–0.4 g/cc/hr.

* * * * *